United States Patent [19]

Sleziona et al.

[11] 4,104,309
[45] Aug. 1, 1978

[54] PHOSPHINE OXIDES HAVING POLYFLUORINATED-CHAIN AND THEIR PREPARATION

[75] Inventors: Joseph Sleziona; Michel Demarcq, both of Lyons, France

[73] Assignee: Produits Chimiques Ugine Kuhlmann, Paris, France

[21] Appl. No.: 537,446

[22] Filed: Jan. 3, 1975

[30] Foreign Application Priority Data

Jan. 3, 1974 [FR] France ............... 74.00108

[51] Int. Cl.² ............................. C07F 9/53
[52] U.S. Cl. .................. 260/606.5 P; 204/158 R
[58] Field of Search ............ 260/606.5 P; 204/158 R

[56] References Cited

U.S. PATENT DOCUMENTS

| 3,020,315 | 2/1962 | Campbell et al. | 260/606.5 P |
| 3,075,018 | 1/1963 | Pummer et al. | 260/606.5 P |
| 3,393,151 | 7/1968 | Dolle et al. | 260/606.5 P |
| 3,396,197 | 8/1968 | Sharts | 260/606.5 P |
| 3,518,311 | 6/1970 | Maier | 260/606.5 P |
| 3,657,352 | 4/1972 | Bad Soden | 260/606.5 P |

OTHER PUBLICATIONS

Chemical Abstracts, 69, 67477d, (1968).
Chemical Abstracts, 72, 121629g, (1970).

Kasolapoff et al., Organic Phosphorus Compounds, Wiley–Interscience, N. Y., v.3, pp. 357-359, (1972).

*Primary Examiner*—Helen M. S. Sneed
*Attorney, Agent, or Firm*—Pennie & Edmonds

[57] ABSTRACT

This invention relates to new products comprising at least one isomer of polyfluorinated-chain phosphine oxide with the general formula (I):

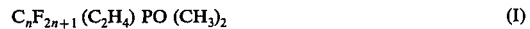

$$C_nF_{2n+1}(C_2H_4)PO(CH_3)_2 \quad (I)$$

and complying with one of the developed formulae II or III :

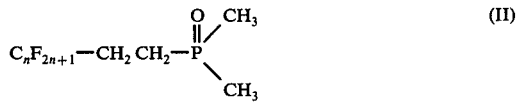

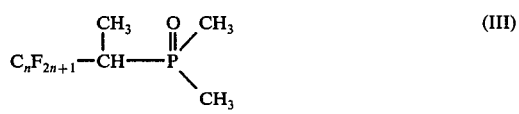

in which $C_nF_{2n+1}$ represents a perfluorinated aliphatic chain, n lying between 2 and 18.

The invention further relates to methods of obtaining the phosphine oxides of formula I.

1 Claim, No Drawings

PHOSPHINE OXIDES HAVING POLYFLUORINATED-CHAIN AND THEIR PREPARATION

A large number of compounds is known having in their molecule a polyfluorinated aliphatic chain and a polar terminal group. These compounds are often very effective surface-acting agents in minimal doses and in spite of their relatively high cost they are used in many applications, for example in the textile industry, the treatment of metals, products for extinguishers, the leather industry, polymerisation of fluorinated resins, polishes, lubricants, and paper manufacture.

A number of compounds exists in which the terminal polar group is a phosphorated radical, for example a phosphonic group — $PO_3H_2$, a phosphoric group — $O - PO_3H_2$, an ester-phosphonic group — $PO(OR)_2$ or an ester-phosphoric group — $O - PO(OR)_2$.

The phosphorated radical may also represent only a part of the terminal polar group, as for example in the compounds $R_F$ — $CON(CH_3)$ — $C_2H_4$ — $O$ $PO_3H_2$ or $R_F$ — $CHOH$ — $CH_2O$ — $PO_3H_2$, where $R_F$ designates a perfluorinated aliphatic radical.

However, no compound of this type has yet been disclosed with, for the terminal polar group, a dimethyl phosphine oxide radical — $PO(CH_3)_2$.

We have found that such compounds are surfactants of astonishing effectiveness, some of which make it possible, for example, to reduce the surface tension of water to values below 15 dynes/cm at a concentration as low as 250 ppm, which are given by only a very small number of other fluorinated surfactants and by none of the known non-fluorinated surfactants.

The fluorinated phosphine oxides of the present invention also have all the properties of the ordinary non-ionic surfactants, that is to say their effectiveness depends very little on the pH of the medium or on the presence of salts in solution. They are also remarkable for their thermal resistance in the anhydrous state, so that, for example, they can be distilled in a vacuum or in solution.

The phosphine oxides of formula (I) can be synthesized by standard methods for preparing phosphine oxides known by those skilled in the art, such as have been described for example in the work by G. M. KOSOLAPOFF and L. MAIER, Organic Phosphorus Compounds, vol. 3, P. 343 to 383.

For example it is possible to oxidize a tertiary phosphine $C_nF_{2n+1}$ — $C_2H_4$ — $P(CH_3)_2$, hydrolyze a dichloro phosphorane $C_nF_{2n+1}$ — $C_2H_4$ — $P(CH_3)_2$ $Cl_2$, perform the MICHAELIS-ARBUZOV transposition on a phosphinous ester $C_nF_{2n+1}$ — $C_2H_4$ — $P(CH_3)$ $(OCH_3)$, or $C_nF_{2n+1}$ — $C_2H_4O$ — $P(CH_3)_2$, decompose in an alkaline medium a phosphonium halide such as $[C_nF_{2n+1}$ — $C_2H_4$ — $P\oplus(CH_3)_2 (CH_2 - C_6H_5), Hal\ominus]$, or again it is possible to react a Grignard reagent $CH_3MgX$ with a phosphonyl chloride $C_nF_{2n+1}$ — $C_2H_4$ — $POCl_2$ or with an ester $C_nF_{2n+1}$ — $C_2H_4$ — $PO(OCH_3)_2$, or a Grignard reagent $C_nF_{2n+1}$ — $C_2H_4MgX$ with dimethyl phosphynil chloride $(CH_3)_2 P(O)Cl$ or with methyl dimethyl phosphinate $(CH_3)_2 P(O)OCH_3$, X being chlorine, bromine or iodine.

The two preferred methods are:

A. condensing a phospho-magnesian derivative $(CH_3)_2P$ — $OMgX$ with an iodide $C_nF_{2n+1}$ — $CH_2CH_2I$ in conformity with the scheme:

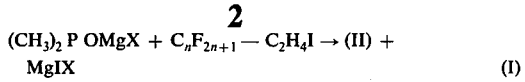

$$(CH_3)_2 P\ OMgX + C_nF_{2n+1} - C_2H_4I \rightarrow (II) + MgIX \qquad (1)$$

where X has the above mentioned meaning;

B. adding dimethyl phosphine oxide $(CH_3)_2 P(O)H$ (also known as dimethyl phosphinous acid) to an olefin $C_nF_{2n+1}$ — $CH = CH_2$ in the presence of free radicals, in confirmity with the scheme:

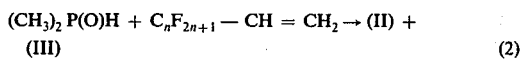

$$(CH_3)_2 P(O)H + C_nF_{2n+1} - CH = CH_2 \rightarrow (II) + (III) \qquad (2)$$

The phospho-magnesian derivative employed in method A is obtained in the conventional manner by reaction of a methyl magnesium halide with a dialkyl phosphite $HPO(OR)_2$ (still called in the Anglo-Saxon nomenclature dialkyl phosphonate), R being preferably a short aliphatic radical such as methyl or ethyl. Reference can be made on this subject to the work by HOUBEN-WEYL, Methoden der Organischen Chemie, Vol. XII/1, page 197 or that of KOSOLAPOFF and MAIER, Organic Phosphorus Compounds, Vol. 4, p. 467.

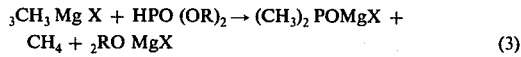

$$_3CH_3 Mg X + HPO(OR)_2 \rightarrow (CH_3)_2 POMgX + CH_4 + {_2}RO\ MgX \qquad (3)$$

The reaction of the phosphorated magnesium with the iodide $C_nF_{2n+1}$ — $C_2H_4I$ must take place in a solvent or mixture of inert solvents consisting preferably, at least in part, of an ether-oxide such as ethyl oxide, isopropyl oxide, butyl oxide, dioxane, tetrahydrofuran, tetrahydropyran, glycol dimethyl ether (glyme), or diethylene-glycol dimethyl ether (diglyme). Reaction (1) may take place at a temperature between −20° and +100° C but preferably between +20 and +60° C. An excess of iodide $C_nF_{2n+1}$ — $C_2H_4I$ which may go up to 100% relative to stoichiometry may be used without disadvantage, most of this excess being recoverable.

To isolate the phosphine oxide of formula (II) formed by the reaction for formula (1) it is possible, for example, to add aqueous hydrochloric acid to the reactive mixture, drive off the organic solvent, extract the phosphine oxide by a suitable solvent which is not water soluble, for example methylene chloride, chloroform, dichloro ethane or trichloro trifluoro ethane, purify the organic solution by washing with an aqueous solution of an alkaline agent such as soda, sodium carbonate, disodium phosphate, or borax, then drive off the solvent and recover the crude phosphine oxide which can then, if necessary, be purified by distillation in a vacuum or by recrystallisation in a solvent.

Synthesis of the phosphine oxides by method (B) can be carried out at a temperature between 0° and 200° C, preferably between 50° and 150° C, and in the presence of a generator of free radicals such as benzoyl peroxide, di-tertiobutyl peroxide, tertiobutyl hydroperoxide, cumene hydroperoxide, tertiobutyl perbenzoate, or lauroyl peroxide, azo-bis (isobutyro nitrile), or under the action of ultra-violet light.

An excess of up to 200% in relation to stoichiometry of one or other of the reagents may be used without disadvantage.

The reaction may take place in an inert solvent but this is not necessary in general.

The mixture of phosphine oxides formed by reaction (2) can be recovered most conveniently by fractional distillation in a vacuum. Since the vapour tensions of the constituents (II) and (III) of this mixture are very close it is very difficult to separate them by distillation; moreover it is generally not necessary to separate them for the applications to which they will be put because their physico-chemical properties are very close.

The products of the invention have numerous applications, for example as wetting agents for aqueous or oily solutions, levelling or anti-streaking agents in polishes or emulsion paints, solvent evaporisation retardants, additives in extinguishers, or mould-release agents.

The invention will now be further described with reference to the following Examples.

EXAMPLE 1

Methyl magnesium bromide was prepared in an agitated Pyrex glass reactor in 250 ml of ethyl ether from 24 g of magnesium shavings (1 gram atom). The solution obtained was diluted with 210 ml of tetrahydrofuran (THF) and then, in the space of 1 hour, 34.5 g of diethyl phosphite (0.25 mol) was poured in, the temperature being kept at 15°–24° C by means of a salt bath. When the liberation of methane stopped the ether was expelled by distillation through a Vigreux column without distilling the THF.

Then 143 g of n-$C_8F_{17}$ — $C_2H_4I$ (0.25 mol) dissolved in 300 ml of THF was added, all at once and with brisk agitation. A slight exothermic effect appeared. After being left for a night at ambient temperature and boiled for 2 hours under reflux the cooled solution was hydrolyzed with the addition of 600 g of crushed ice and 100 ml of concentrated hydrochloric acid, after which most of the THF was expelled by distillation. The petrolatum residue was taken off by 500, 300, 100, 100, 100 and 100 ml of tepid chloroform in succession. The chloroform solutions were combined and cooled and then filtered and subsequently washed with 400 ml of a 7% aqueous solution of $K_2CO_3$. After evaporation of the organic phase solvent a residue of phosphine oxide in the crude state was obtained which weighed 83 g. This was vacuum distilled, giving 75 g of phosphine oxide $C_8F_{17}$ — $CH_2CH_2$ — $PO(CH_3)_2$ distilling at 124°–125° C under 1.05 torrs. This is a colourless solid melting at 99°–100° C. Mass spectrometry confirms the theoretical molecular mass of 524 (traces of heavier phosphine oxides are also present:

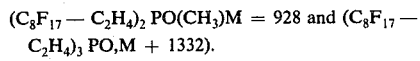

$(C_8F_{17} - C_2H_4)_2 PO(CH_3)M = 928$ and $(C_8F_{17} - C_2H_4)_3 PO, M + 1332)$.

The 250 ppm aqueous solution of the resultant phosphine oxide has a surface tension equal to 14.3 dynes/cm at 25° C.

EXAMPLE 2

The method of operation in Example 1 was repeated using the iodide n—$C_6F_{13}$— $C_2H_4I$. Solid hygroscopic phosphine oxide $C_6F_{13}$ — $CH_2 CH_2$ — $PO(CH_3)_2$, was obtained which melted at 76°–79° C and distilled at 99°–101° C under 0.25 torr.

The 250 ppm aqueous solution has a surface tension equal to 14.7 dynes/cm at 26° C.

EXAMPLE 3

The method of operation in Example 1 was repeated using the iodide n—$C_4F_9$ — $C_2H_4I$ and replacing the diethyl phosphite mol for mol by dimethyl phosphite. The very hygroscopic, solid phosphine oxide $C_4F_9$ — $CH_2 CH_2$ — $PO(CH_3)_2$, was obtained which melted at approximately 41° C and distilled at 106°–112° C under 1 torr.

Its 250 ppm aqueous solution has a surface tension equal to 28.7 dynes/cm at 25° C.

EXAMPLE 4

The method of operation in Example 1 was repeated, using the iodide n — $C_{10}F_{21}$— $C_2H_4I$ and purifying the phosphine oxide not by distillation this time, but by recrystallisation in benzene. Solid phosphine oxide $C_{10}F_{21}$— $CH_2 CH_2$ — $PO(CH_3)_2$, was obtained, which melted at 118° C and the purity of which was checked by chromatography in the gaseous phase, by mass spectrometry and by dosage of the phosphorus (found: P% = 4.78; calculated = 4.97).

Its aqueous solution at 250 ppm has a surface tension equal to 37.2 dynes/cm at 23° C and 17 dynes/cm approximately at 55° C.

EXAMPLE 5

In an agitated glass reactor there were placed 346 g (1 mol) of olefin $C_6F_{13}$ — $CH = CH_2$ and 39 g (0.5 mol) of dimethyl phosphine oxide $(CH_3)_2 P(O)H$ which had been freshly rectified. The gas was removed from the mixture in a vacuum at 70° C and then the vacuum was broken with nitrogen and 2.3 g of azobis isobutyro nitrile (AIBN) was added. The temperature was kept at 70°–74° C for 24 hours under nitrogen adding further doses of the same amount of AIBN after 8 hours and 16 hours, respectively. The final mixture was rectified in a vacuum giving 139 g of a hygroscopic solid distilling around 105° C under 0.5 torr and melting between 60° and 74° C. The NMR proton spectrum of the product dissolved in deuterated pyridine indicates that it consists essentially of a mixture of the two phosphine oxides II and III (n = 6) in the ratio II/III = g5/5 approximately.

The 250 ppm aqueous solution of this compound has a surface tension equal to 16.0 dynes/cm at 23° C.

What we claim is:

1. New products comprising at least one isomer of polyfluorinated-chain phosphine oxides with the general formulae II or III:

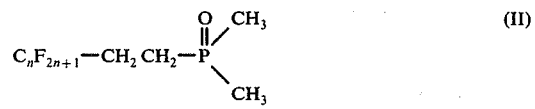

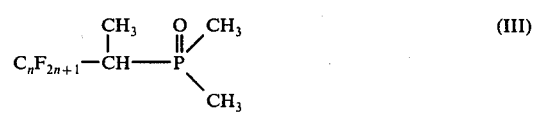

in which $C_nF_{2n+1}$ represents a perfluorinated aliphatic chain, n lying between 2 and 18.

* * * * *

UNITED STATES PATENT AND TRADEMARK OFFICE
CERTIFICATE OF CORRECTION

PATENT NO. : 4,104,309
DATED : August 1, 1978
INVENTOR(S) : Joseph Sleziona and Michel Demarcq It is certified that error appears in the above-identified patent and that said Letters Patent are hereby corrected as shown below:

Column 4, line 43, reads "g5/5", should read
--95/5--

Signed and Sealed this

Thirteenth Day of March 1979

[SEAL]

Attest:

RUTH C. MASON
*Attesting Officer*

DONALD W. BANNER
*Commissioner of Patents and Trademarks*